(12) United States Patent
Boudin et al.

(10) Patent No.: US 10,119,863 B2
(45) Date of Patent: Nov. 6, 2018

(54) FLASH THERMOGRAPHY PHOTOBOX

(71) Applicant: Siemens Energy, Inc., Orlando, FL (US)

(72) Inventors: Dustin C. Boudin, Belmont, NC (US); Clifford Hatcher, Jr., Orlando, FL (US); Anand A. Kulkarni, Charlotte, NC (US); Ahmed Kamel, Orlando, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 128 days.

(21) Appl. No.: 15/344,750

(22) Filed: Nov. 7, 2016

(65) Prior Publication Data

US 2018/0128687 A1    May 10, 2018

(51) Int. Cl.
| | |
|---|---|
| *G01K 15/00* | (2006.01) |
| *G01N 25/00* | (2006.01) |
| *G01J 5/00* | (2006.01) |
| *G01K 13/00* | (2006.01) |
| *G01K 1/00* | (2006.01) |
| *F01D 21/00* | (2006.01) |

(Continued)

(52) U.S. Cl.
CPC .......... *G01J 5/0088* (2013.01); *F01D 21/003* (2013.01); *G01J 5/10* (2013.01); *G01N 25/72* (2013.01); *F01D 5/288* (2013.01); *F01D 9/023* (2013.01); *F05D 2220/32* (2013.01); *F05D 2240/35* (2013.01); *G01J 2005/0077* (2013.01); *G01J 2005/0081* (2013.01); *G06T 2207/10048* (2013.01); *G06T 2207/30164* (2013.01)

(58) Field of Classification Search
USPC .......... 374/141, 4, 45, 121, 208, 144, 1, 166
See application file for complete search history.

(56) References Cited

U.S. PATENT DOCUMENTS

| | | |
|---|---|---|
| 2011/0125423 A1 | 5/2011 | Allen et al. |
| 2013/0026365 A1 | 1/2013 | Jahnke et al. |

(Continued)

FOREIGN PATENT DOCUMENTS

EP    2881731 A1    6/2015

OTHER PUBLICATIONS

PCT International Search Report and Written Opinion of International Searching Authority dated Jan. 31, 2018 corresponding to PCT International Application No. PCT/US2017/058941 filed Oct. 30, 2017.

*Primary Examiner* — Mirellys Jagan

(57) ABSTRACT

A system for automated condition assessment of a turbine component is provided. The system includes a partially enclosed photobox and a controller. The partially enclosed photobox includes a configurable rotational table adapted to carry the turbine component, at least one wall perpendicular to and abutting a horizontal platform upon which the rotational table is carried. The photobox also includes a plurality of cameras configured to be automatically positioned at locations surrounding the turbine component and capture images of the turbine component. The controller communicates with each of the cameras to respectively control the positioning of each camera in order to capture a desired view of the turbine component. At least one of the cameras is an infrared camera configured to perform flash thermography capturing a thermographic image of a portion of the turbine component. The thermographic image is used to assess the condition of the turbine component.

14 Claims, 4 Drawing Sheets

(51) Int. Cl.
    *G01J 5/10*     (2006.01)
    *G01N 25/72*    (2006.01)
    *F01D 5/28*     (2006.01)
    *F01D 9/02*     (2006.01)

(56) References Cited

U.S. PATENT DOCUMENTS

2015/0355074 A1  12/2015  Zhou et al.
2016/0372602 A1  12/2016  Luo
2017/0359530 A1  12/2017  Boudin et al.

FLASH THERMOGRAPHY PHOTOBOX

BACKGROUND

1. Field

The present disclosure relates generally to a method and system for non-destructive inspection of components, and more particularly, to a method and system for automatic non-destructive inspection of turbine components using flash thermography.

2. Description of the Related Art

In many industrial applications, non-destructive testing methods are used to evaluate components without causing damage. One such application of non-destructive testing uses flash thermography to test components of a turbine engine such as a turbine blades or vanes, combustor baskets, or a transition component. These components frequently consist of a substrate coated with a thermal barrier coating that protects the substrate from high temperatures and a corrosive environment. For example, coated gas turbine components may require testing to determine the thickness of the thermal barrier coating or whether the coating has any delaminations, sections where the coated layer has become separated from the substrate. A delaminated layer may cause component failure during normal operation of the turbine.

Currently, inspection and testing of coated turbine components may be done using flash thermography, a commonly used non-destructive testing method in which the surface of the component is heated by a light pulse typically lasting only a few milliseconds. Under normal conditions, the part cools after flash heating, as the heat deposited at the surface flows toward the cooler interior. However, internal anomalies in the test piece, such as voids, inclusions, delamination, moisture, or changes in thickness or density, cause changes in the cooling rate at the surface. An infra-red camera is then used to capture infra-red radiation emitted by the component to form a thermographic image. The internal anomalies as referenced above would be visible in the thermographic image.

In order to capture images of the multitude of three dimensional surfaces of a component such that the images of the entire surface or nearly the entire surface are captured, a plurality of optical cameras, including perhaps a mixture of infrared and visible light cameras, are manually positioned around the coated surfaces of the component. The current method of imaging components using flash thermography involves a lengthy manual set up and positioning of the cameras relative to the component and the desired area of inspection. Two dimensional data is obtained from the images which are then correlated back to the three dimensional component. Having to manually set up the cameras for each required image requires a lot of time and manpower. Thus, an automatic inspection method reducing the time and manpower required for the current method of manually setting up a plurality of cameras for each required image of a component is desired.

SUMMARY

Briefly described, aspects of the present disclosure relates to a system for automated condition assessment of a turbine component and a non-destructive method for automatic condition assessment of a turbine component.

A system for automated condition assessment of a turbine component is provided. The system includes a partially enclosed photobox and a controller. The partially enclosed photobox includes a configurable rotational table adapted to carry the turbine component, at least one wall perpendicular to and abutting a horizontal platform upon which the rotational table is carried. The photobox also includes a plurality of cameras configured to be automatically positioned at locations surrounding the turbine component and capture a plurality of images of the turbine component. The controller communicates with each of the cameras to respectively control the positioning of each camera in order to capture a desired view of the turbine component. At least one of the plurality of cameras is an infrared camera configured to perform flash thermography capturing a thermographic image of a portion of the turbine component. The thermographic image is used to assess the condition of the turbine component.

A non-destructive method for automatic condition assessment of a turbine component is provided. The method includes providing a plurality of optical cameras, each camera having a field of view of the turbine component. At least one of the optical cameras is an infrared camera configured to perform flash thermography. A three dimensional model is created by the controlled from obtained images of the turbine component against a photographable calibration target. The plurality of cameras are automatically positioned around the turbine component by the controller in the photobox in order to capture at least one image of a desired view of the turbine component. A plurality of images are captured by the plurality of cameras. The plurality of images are stitched by the controller onto the three dimensional model. The stitched image is used to analyze a characteristic of the turbine component.

DETAILED DESCRIPTION

To facilitate an understanding of embodiments, principles, and features of the present disclosure, they are explained hereinafter with reference to implementation in illustrative embodiments. Embodiments of the present disclosure, however, are not limited to use in the described systems or methods.

The components and materials described hereinafter as making up the various embodiments are intended to be illustrative and not restrictive. Many suitable components and materials that would perform the same or a similar function as the materials described herein are intended to be embraced within the scope of embodiments of the present disclosure.

Figure 1:
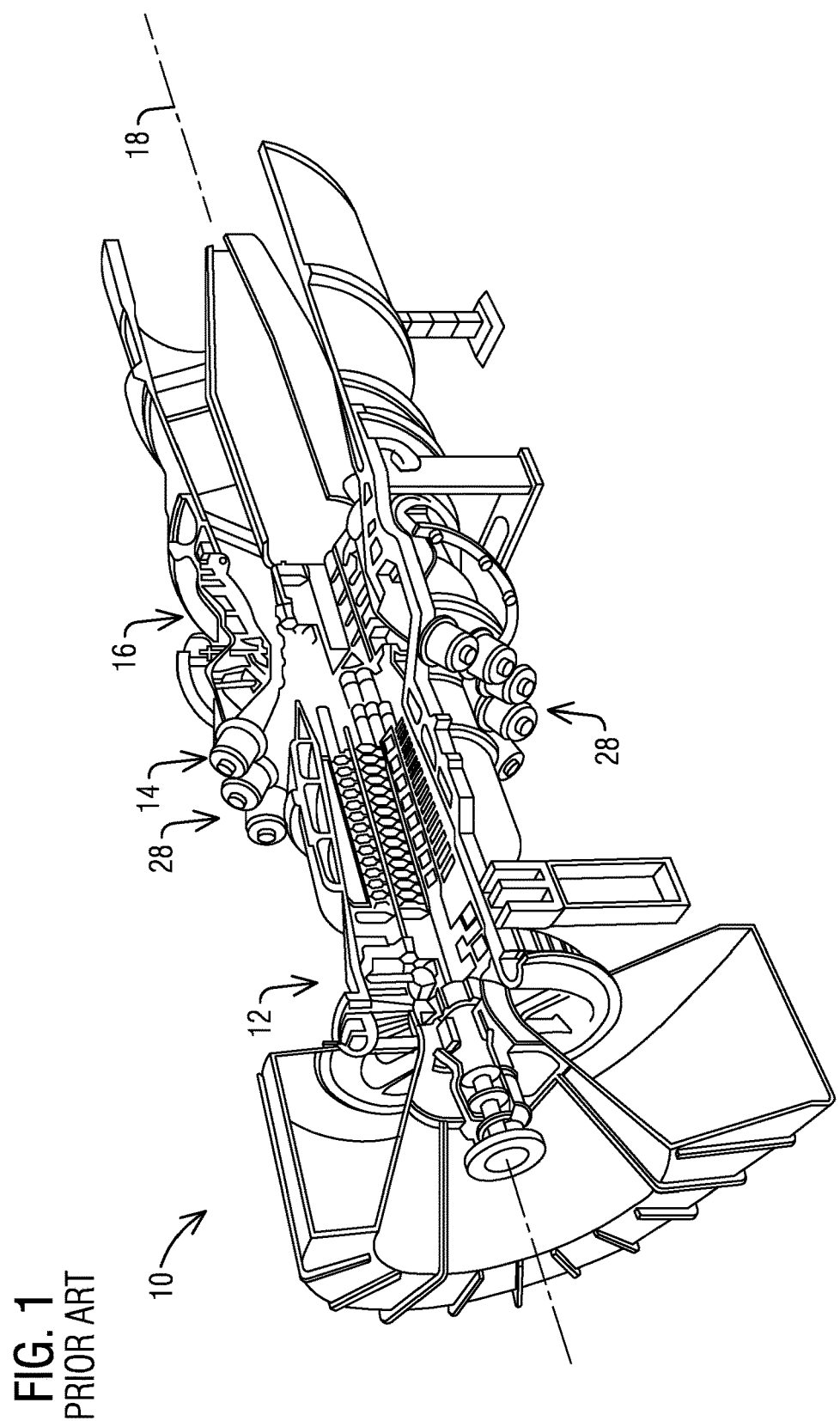
FIG. 1 illustrates a side partial cross sectional view of an axial flow gas turbine.

Referring to FIG. 1, an industrial gas turbine engine 10 is shown. The engine 10 includes a compressor section 12, a combustor section 14, and a turbine section 16 arranged along a horizontal center axis 18. The combustor section 14 includes a plurality of combustors 28. A hot working gas is conveyed from the combustor section 14 through to the turbine section 16.

Sections of the turbine 10 that are exposed to the hot gases as the gases travel along a hot gas path in the turbine 10 may include a ceramic-based coating that serves to minimize exposure of the base metal of a component, such as an airfoil base metal, to high temperatures that may lead to oxidation of the base metal. Such a coating may be a known thermal barrier coating (TBC) that is applied onto a bond coating formed on the base metal.

A turbine 10 is typically operated for extended periods. The TBC layer or both the TBC and bond coat layers may undesirably deteriorate or delaminate during operation of the turbine 10. This exposes the base metal to high temperatures, which may lead to oxidation of the base metal. The turbine 10 is inspected at periodic intervals to check for wear damage and other undesirable conditions that may have occurred with respect to various internal components. In addition, the TBC and bond coat layers are routinely inspected to determine the degree of deterioration of the TBC and bond coat layers (i.e., remaining thickness of the layers) and other undesirable conditions when the turbine engine is shut down or prior to assembly.

Figure 2:
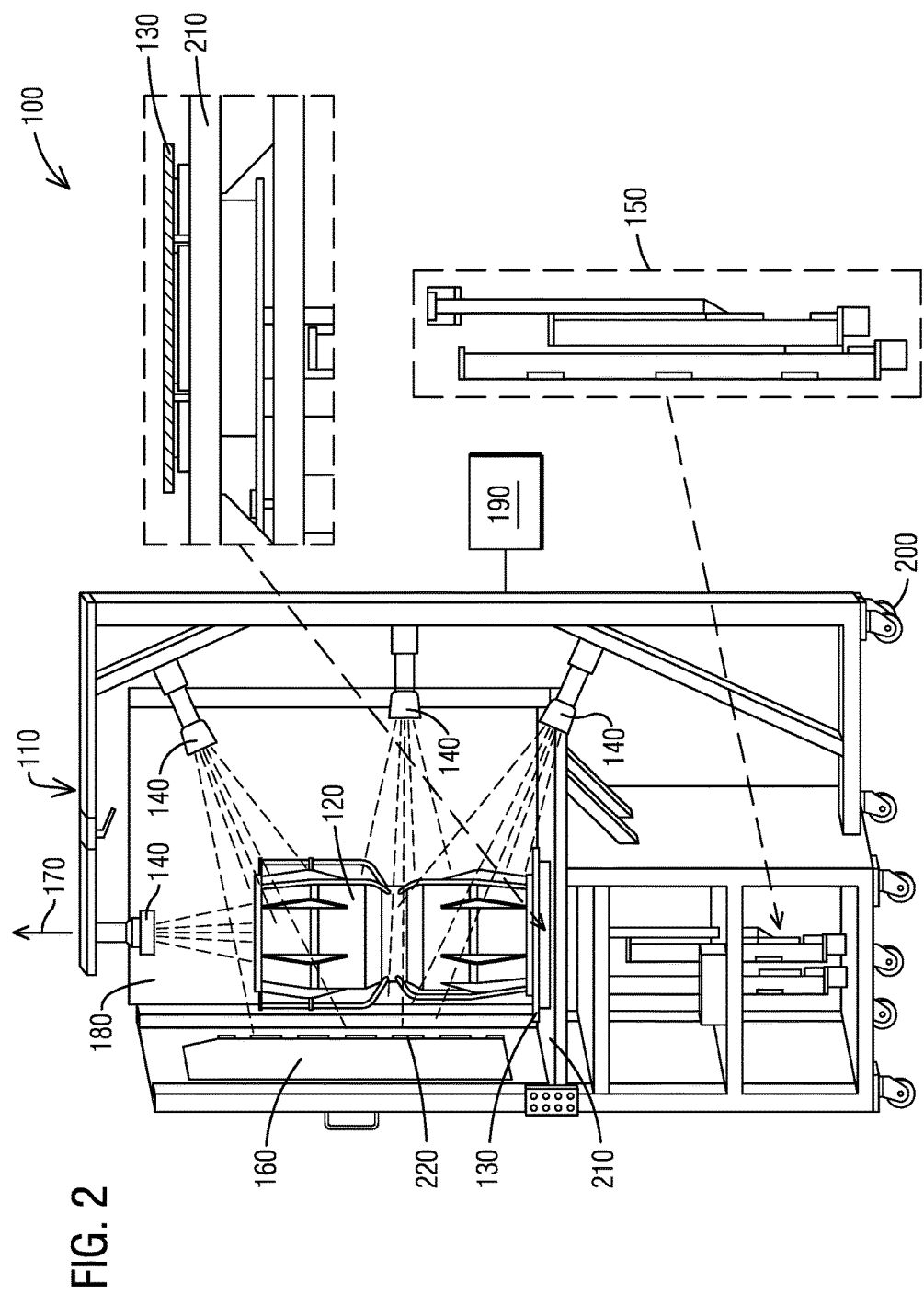
FIG. 2 illustrates a perspective view of a photobox in accordance with an embodiment.

Referring now to FIG. 2, a photobox 100 is illustrated. The photobox 100 is an automated image capturing device for the non-destructive inspection of a turbine component 120. In the example shown in FIG. 2, the turbine component 120 is a combustor basket. However, the turbine component 120 may also be a combustor transition, a turbine blade or vane, or any other coated component. The photobox 100 includes a rotational table 130 adapted to accommodate the specific turbine component 120. In the shown embodiment, a plurality of walls 180 partially enclose the turbine component 120. Surrounding the turbine component 120 on the interior of at least one wall 180, a plurality of optical cameras 140 are positioned and configured to be automatically controlled by a controller 190. The controller 190 may be a generic computer or a module of a generic computer.

Figure 3:
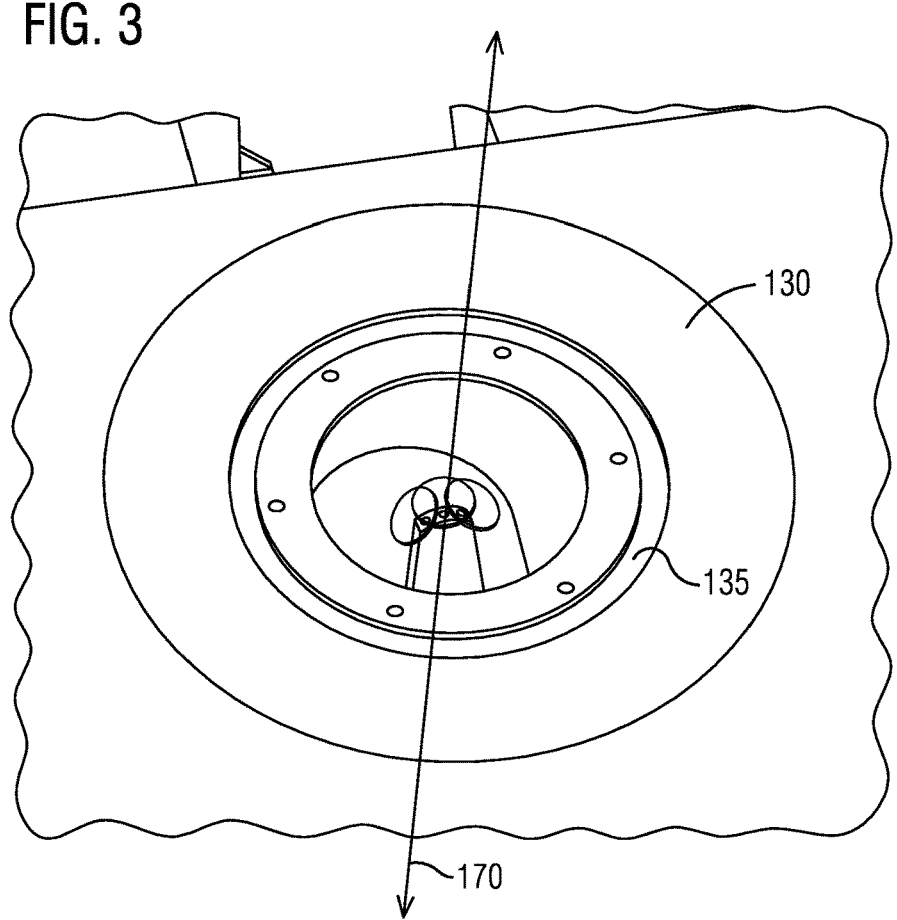
FIG. 3 illustrates a perspective view of a rotational table.

FIG. 3 illustrates a perspective view of a rotational table 130 configured to carry a combustor basket. In the illustrated embodiment, the rotational table 130 upon which the turbine component 120 is carried includes machined grooves 135 adapted to accommodate a particular turbine component such as a combustor transition. With the turbine component seated into the machined grooves, the rotational table 130 securely holds the combustor transition in position. For the purpose of imaging, the rotational table 130 allows a rotational movement about a vertical axis 170 as shown in FIG. 2.

The rotational table 130 is powered by a motor, the motor controlled by the controller 190. The vertical position of the rotational table 130 may be controlled by a motorized linear stage 150, as shown in FIG. 2, also controlled by the controller 190.

The photobox 100 includes at least one wall 180 which is essentially perpendicular to and abuts a platform 210 that carries the rotational table 130 such that the turbine component 120 is partially enclosed by the at least one wall 180. The at least one wall 180 includes diffused lighting in order to eliminate glare that may appear in the images. In an embodiment, one of the at least one wall 180 may include a door 160 to the partially enclosed photobox 100 for easier access to the turbine component 120

In an embodiment, the photobox 100 includes wheels 200, at least one at each corner in the illustrated embodiment of FIG. 2, attached to the bottom of the photobox 100 for mobility such that the photobox 100 may be easily moved from one inspection area to another.

Referring back to the illustrated embodiment shown in FIG. 2, a plurality of cameras 140 is positioned surrounding the turbine component 120. The number of cameras surrounding the turbine component may lie in a range of 2 to 8, for example. In the shown embodiment, four cameras 140 are positioned at vertical positions along a vertical beam and each include a field of view of at least a portion of the turbine component 120. However, the cameras 140 may be positionable in other configurations around the particular turbine component such that a desired view of the component may be captured in an image. In order to position the cameras in a desired position, motorized linear stages 150 may be used. Also shown in FIG. 2 is a camera 140 positioned downward to include a top view of the turbine component 120. In order to position this downward facing camera 140 in a position including a desired field of view above the turbine component 120, a swing away beam 110 carries the camera. The swing away beam 110 may be attached to the vertical beam such that it may rotate relative to the vertical beam. In an embodiment, the controller 190 may automatically position the swing away beam 110 so that the camera has a desired field of view.

Additionally, a camera 140 may be attached to a motorized linear stage 150 configured to move the camera 140 vertically into the interior of a hollow turbine component 120 in order to capture images of the interior of the hollow turbine component 120. The linear stage 150 includes an attachment portion to which the camera 140 may be attached. The attached camera 140 may be a 360 degree visible camera such that a 360 degree view of the interior of the hollow turbine component 120 may be obtainable. In an alternate embodiment, the camera 140 may be an infrared camera for thermographic imaging.

In an embodiment, the at least one wall 180 includes a two dimensional calibration target 160 which may be used to register in three dimensional space the position of the turbine component 120 so that the controller 190 may create a three dimensional model of the component 120. The shape of the two dimensional calibration target 160 corresponds to the shape of the component 120. In an embodiment the calibration target 160 is disposed on the door 220 of the photobox 100 opposite the plurality of cameras 140 so that the component 120 may be imaged against the calibration target 160. These calibration images of the component 120 taken against the calibration target 160 are used by the controller 190 to stitch the captured images of the component 120 onto the 3D model of the component. The stitched data image will be used for analysis of the component 120.

The plurality of cameras 140 may include visible cameras, infrared cameras, or a combination of visible cameras and infrared cameras. The plurality of visible cameras may include high resolution cameras. Infrared cameras may be a part of a flash thermography system. In an embodiment 5 or 6 cameras may be arranged surrounding the component in order to capture both visible images as well as thermographic images of the component 120. The plurality of cameras 140 each capture at least one image of a desired view of the turbine component 120. The controller 190 compiles the captured images and stitches the images onto the three-dimensional model of the turbine component 120.

Figure 4:
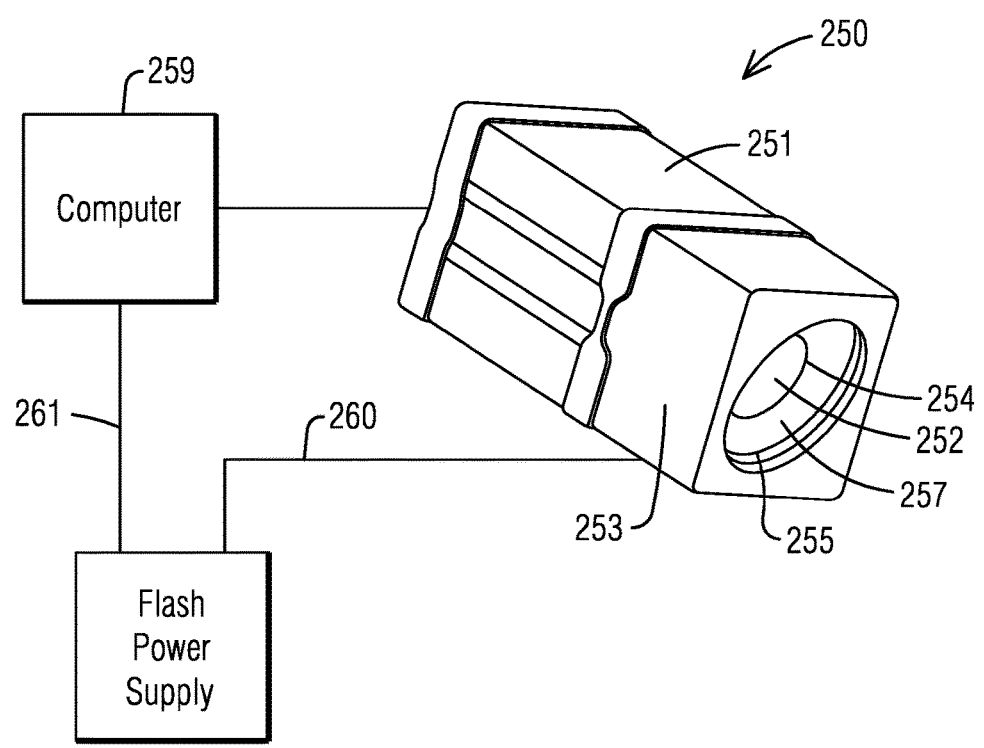
FIG. 4 illustrates a flash thermography device for imaging a turbine component.

Referring to FIG. 4, a flash thermography device 250 for imaging a turbine component 120 in accordance with an embodiment is shown. The device 250 includes an infrared sensor portion 251 for detecting thermal energy in the infrared region of the electromagnetic spectrum. In an embodiment, the IR sensor 251 is an IR camera having a lens 252 although it is understood that other types of IR sensors may be used. The device 250 is configured to capture IR images of a turbine component 120.

The device 40 also includes a flash enclosure 253 having an enclosure aperture 254 that exposes the lens 252 to enable detection of thermal energy by the IR sensor 251. A flash source 255 is located around a periphery of the enclosure aperture 254. In an embodiment, the flash source 255 has an annular shape that includes a flash aperture 256 that is aligned with the enclosure aperture 254 and the lens 252. The flash source 255 may be configured as a flash tube although it is understood that other types of flash sources may be used. The flash enclosure 253 may also include a substantially cone shaped reflector 257. The device 250 further includes a flash power supply 258 connected between a computer 259 and the flash source 255 by electrical connections 260. The flash source 255 is energized by the flash power supply 258 thereby causing the flash source 255 to emit a light pulse that heats a component, such as a turbine component 120. A portion of the thermal energy radiated by the component travels through the enclosure 254 and flash apertures 256 and is detected by the IR sensor 251. The IR sensor 251 generates IR images of the component based on the thermal energy radiated by the component. The IR sensor 251 may also be configured to obtain image data at other frequencies in addition to or in place of the infrared region of the electromagnetic spectrum. The IR sensor 251 is communicatively coupled to the computer 259 by an electrical connection 261 or a wireless connection.

The provided system for the automated condition assessment of turbine components includes the previously described photobox 100 including the plurality of cameras 140 and a controller 190. The controller 190 is communicatively coupled to the cameras 140, the motorized rotational table 130, as well as the motorized linear stages 150. The controller 190 may be a computer, or a module of a computer, that includes software and drivers for controlling the positioning of the cameras 140 as well as the motors controlling the rotational table 130 and linear stages 150. The positioning of the cameras 140 may be preprogrammed into the computer for each individually tested component or each type of component, such as for example, a combustor basket. At least one of the cameras is an infrared camera configured to perform flash thermography.

Figure 5:
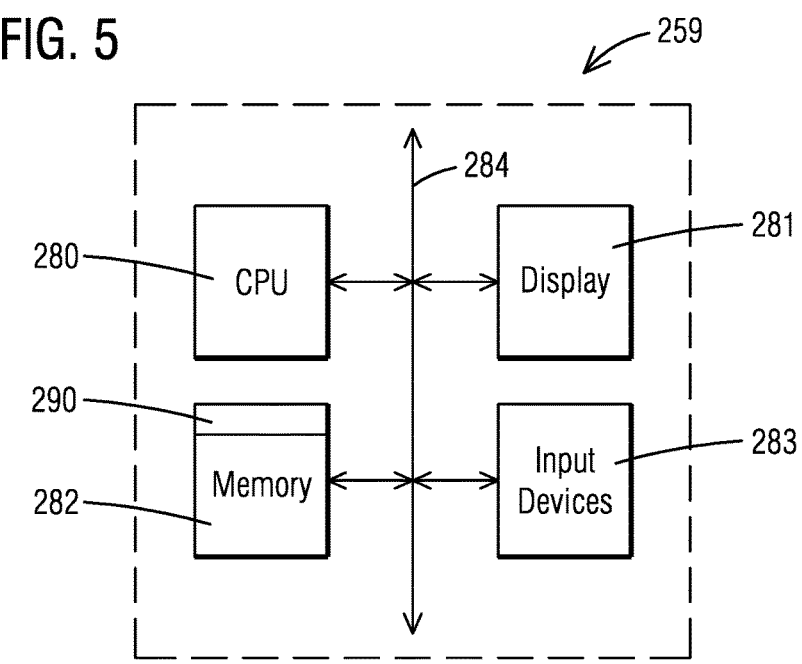
FIG. 5 illustrates a high level block diagram of a computer.

The computer 259, as illustrated in FIG. 5, may include a central processing unit 280, a memory 282, and an input/output interface 284. The computer is generally coupled through the I/O interface 284 to a display 281 for visualization and various input devices 283 that enable user interaction with the computer 259 such as a keyboard. For example, from the I/O interface 284 a user may load the component 120 into the computer 259 by identifying the type of component to be inspected. Using the identified type of component, the controller 190 may automatically position the cameras 140 according to pre-programmed positions stored in memory 282 in order to capture a desired image.

Referring to FIGS. 1-5, a non-destructive method for automatic inspection of a turbine component 120 is also provided. A plurality of optical cameras 140 are provided and configured to capture a desired image of the turbine component 120. As described above the plurality of cameras 140 may be strategically positioned at fixed points or on movable motorized linear stages surrounding the turbine component 120 so that a desired view of the component 120 may be captured by the cameras 140 producing a two dimensional image.

A user may then position a turbine component 120 onto a motorized rotatable table 130. The motorized rotatable table 130 is in communication with the controller 190 which may control the positioning of the rotatable table 130 about a vertical axis 170, thus also rotating the component about the vertical axis 170, to a desired position. The specific turbine component 120 may be loaded into the computer 259 by the user using an I/O interface 282 on the computer 259.

Prior to capturing the two dimensional images of the turbine component 120, a three dimensional model of the component 120 is created by a controller 190. This is accomplished using a calibration target 160 including a two dimensional outline of the turbine component 120. Images are captured using the visible light cameras 140 of the component 120 against a photographable calibration target 160. These images are used by the controller 190 to stitch captured images onto the three dimensional model as textures.

In an embodiment, the computer 259 automatically controls the positioning of the cameras using pre-programmed locations stored in the memory 282 of the computer 259. In an alternate embodiment, the cameras may be manually positioned by the user. Using the plurality of cameras 140, which may include visible light and/or infrared cameras, at least one image of the component 120 is captured and stored in the computer 259. The computer 259 uses the two dimensional images captured from the camera to stitch the images onto the three dimensional model creating a virtual and interactive model of the turbine component 120.

The acquired data may be analyzed in order to assess the condition of the turbine component 120. Assessing the condition of the turbine component 120 may include determining defects on the component such as delaminations. Defects or discontinuities will show up in a thermographic image as a different temperature change than normal surface or subsurface conditions. Also, one may assess the condition of the turbine component by measuring the thickness of a thermal barrier coating on the substrate of the turbine component 120. In an embodiment, a user may be able to track the thickness of the thermal barrier coating on the component 120 at different inspection intervals during its lifetime.

The above described system and method automates a process that has traditionally been done manually, reducing the time and cost to manually set up the testing environment including the multitude of positions each camera may need to take for each desired field of view of the turbine component. In addition, using pre-programmed settings for each camera allows a desired view to be repeatable such that images taken at different times may be accurately compared. It may be appreciated that the data gathered on the individual components may be stored and referenced for future use, such as for example, statistical analysis on the component. The statistical data may be used by the controller to track the health of the component over time.

While embodiments of the present disclosure have been disclosed in exemplary forms, it will be apparent to those skilled in the art that many modifications, additions, and deletions can be made therein without departing from the spirit and scope of the invention and its equivalents, as set forth in the following claims.

What is claimed is:

1. A system for automated condition assessment of a turbine component, comprising:
    a partially enclosed photobox, comprising:
        a configurable rotational table adapted to carry the turbine component;

at least one wall, the at least one wall essentially perpendicular to and abutting a horizontal platform upon which the rotational table is carried;

a plurality of cameras configured to be automatically positioned at locations surrounding the turbine component and capture a plurality of images of the turbine component; and a controller communicating with each of the plurality of cameras to respectively control the positioning of each camera in order to capture an image of a desired view of the turbine component;

a calibration target disposed on the at least one wall, wherein the calibration target comprises a photographable target, wherein at least one of the plurality of cameras is an infrared camera configured to perform flash thermography capturing a thermographic image of a portion of the turbine component, wherein the thermographic image is used by the controller to assess the condition of the turbine component, and wherein a visible light camera of the plurality of cameras captures images of the calibration target prior to capturing an image of the turbine component in order to create a three dimensional model of the turbine component.

2. The system as claimed in claim 1, wherein the infrared camera of the plurality of cameras and a flash tube are integrated into a single package such that the view is through the center of the flash tube.

3. The system as claimed in claim 1, wherein at least one of the plurality of cameras is a visible light camera.

4. The system as claimed in claim 1, wherein the turbine component is selected from the group consisting of a turbomachine blade or vane, a transition, and a combustor basket.

5. The system as claimed in claim 1,
wherein the controller comprises an I/O interface enabling a user to indicate a specific turbine component to be inspected, and
wherein the controller positions the plurality cameras according to preprogrammed locations which are assigned according to the turbine component to be inspected.

6. The system as claimed in claim 1, wherein the turbine component includes a thermal barrier coating and/or a bond coating.

7. The system as claimed in claim 1, further comprising a linear stage configured to vertically position the rotational table.

8. The system as claimed in claim 7,
wherein the linear stage includes an attachment portion to which a camera of the plurality of cameras is attached, and
wherein the liner stage enables the positioning of the camera with the interior of a hollow turbine component in order to capture an image of the interior of the hollow turbine component.

9. The system as claimed in claim 1, wherein the controller compiles the plurality of images taken by the plurality of cameras and stitches the images onto the three dimensional model of the turbine component.

10. The system as claimed in claim 9, wherein the images stitched onto the three dimensional model are used to visually assess the condition of the turbine component.

11. A non-destructive method for automatic condition assessment of a turbine component, comprising:
providing a plurality of optical cameras, each having a field of view of the turbine component, wherein at least one of the optical cameras is an infrared camera configured to perform flash thermography;
creating, by a controller, a three dimensional model of the turbine component positioned in a photobox from obtained images of the turbine component against a photographable calibration target;
automatically positioning a plurality cameras by the controller around the turbine component in the photobox in order to capture at least one image of a desired view of the turbine component;
capturing a plurality of images of the component from the plurality of cameras;
stitching by the controller the plurality of images onto the three dimensional model of the turbine component;
analyzing a characteristic of the turbine component on the stitched image.

12. The method as claimed in claim 11, further comprising automatic positioning of the turbine component by the controller which is accomplished by controlling a motorized rotational stage upon which the turbine component is carried.

13. The method as claimed in claim 11, wherein the automatic positioning of the plurality of cameras includes controlling the positioning of a 360 degree camera into an interior of a hollow turbine component through control of a linear stage upon which the camera is carried.

14. The method as claimed in claim 11, further comprising obtaining a thermographic image of the turbine component generated by flash heating a surface of the turbine component and capturing by an infrared camera the infra-red radiation emitted from the turbine component.

* * * * *